(12) United States Patent
Bartra Sanmartí et al.

(10) Patent No.: US 8,680,284 B2
(45) Date of Patent: Mar. 25, 2014

(54) PREPARATION PROCESS OF THE SODIUM SALT OF ESOMEPRAZOLE

(75) Inventors: Marti Bartra Sanmartí, Barcelona (ES); Ramón Berenguer Maimó, Barcelona (ES); Joan Gabriel Solsona Rocabert, Barcelona (ES)

(73) Assignee: Esteve Quimica, S.A., Barcelona (ES)

( * ) Notice: Subject to any disclaimer, the term of this patent is extended or adjusted under 35 U.S.C. 154(b) by 0 days.

(21) Appl. No.: 13/577,827

(22) PCT Filed: Feb. 11, 2011

(86) PCT No.: PCT/EP2011/052026
§ 371 (c)(1),
(2), (4) Date: Aug. 8, 2012

(87) PCT Pub. No.: WO2011/098553
PCT Pub. Date: Aug. 18, 2011

(65) Prior Publication Data
US 2012/0309976 A1    Dec. 6, 2012

Related U.S. Application Data

(60) Provisional application No. 61/313,874, filed on Mar. 15, 2010.

(30) Foreign Application Priority Data

Feb. 12, 2010   (EP) .................................... 10382032

(51) Int. Cl.
*A61K 31/44*   (2006.01)
*C07D 401/00*   (2006.01)

(52) U.S. Cl.
USPC ...................................... 546/273.7; 514/338

(58) Field of Classification Search
CPC .............................. C07D 401/00; A61K 31/44
See application file for complete search history.

(56) References Cited

U.S. PATENT DOCUMENTS

2007/0259921 A1 * 11/2007 Bolugoddu et al. .......... 514/338

FOREIGN PATENT DOCUMENTS

| WO | WO94/27988 A1 | 12/1994 |
|----|----|----|
| WO | WO96/25235 A1 | 8/1996 |
| WO | WO 03/089408 A2 * | 10/2003 |
| WO | WO03/089408 A2 | 10/2003 |
| WO | WO2004/002982 A2 | 1/2004 |
| WO | WO2004/052882 A1 | 6/2004 |
| WO | WO2006/001753 A1 | 1/2006 |
| WO | WO2007/012650 A1 | 2/2007 |
| WO | WO2007/013743 A1 | 2/2007 |
| WO | WO2008/149204 A1 | 12/2008 |
| WO | WO2009/040825 A1 | 4/2009 |

OTHER PUBLICATIONS

Sodium methoxide solution 30% w/v, Material Safety Data Sheet (MSDS), Sigma Aldrich, 2012.*
International Search Report and Written Opinion of the International Searching Authority Search Report Application No. PCT/EP2011/052026 issued by the European Patent Office, Netherlands, Rijswijk, dated Mar. 29, 2011.

* cited by examiner

*Primary Examiner* — Rita Desai
*Assistant Examiner* — Ben S Michelson
(74) *Attorney, Agent, or Firm* — Peter B. Scull; Hamilton DeSanctis & Cha LLP

(57) ABSTRACT

A preparation process of esomeprazole sodium substantially free of sulfone impurity including the steps of: a) combining either esomeprazole with a ($C_3$-$C_8$)-ketone or a mixture thereof, a sodium alkoxide, and a ($C_1$-$C_5$)-alcohol, or esomeprazole sodium with a ($C_3$-$C_8$)-ketone or a mixture thereof and a ($C_1$-$C_5$)-alcohol; and b) recovering the esomeprazole sodium formed from the reaction media by filtration.

20 Claims, No Drawings

PREPARATION PROCESS OF THE SODIUM SALT OF ESOMEPRAZOLE

This application is a national phase application under 35 USC 371 of PCT application, PCT/EP2011/052026 filed 11 Feb. 2011 which claims the benefit of European Patent Application No 10382032 filed 12 Dec. 2010 and U.S. Provisional Patent Application Ser. No 61313874 filed 15 Mar. 2010.

FIELD

The present invention relates to a process for preparing esomeprazole sodium substantially free from sulfone impurity (5-methoxy-2-[(S)-[(4-methoxy-3,5-dimethyl-2-pyridinyl)methyl]sulfonyl]-1H-benzimidazole) using a specific combination of solvents and sodium source.

BACKGROUND

Esomeprazole is the International Non-Proprietary Name (INN) of the chemical compound 5-methoxy-2-[(S)-[(4-methoxy-3,5-dimethyl-2-pyridinyl)methyl]sulfinyl]-1H-benzimidazole. The CAS number for esomeprazole is 119141-88-7 and the CAS number for its sodium salt is 161796-78-7. The chemical structure of the esomeprazole sodium is included below:

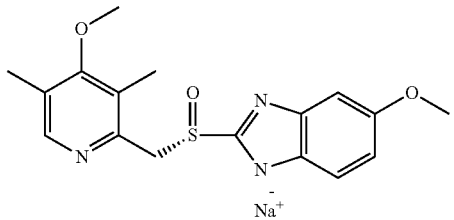

Esomeprazole and its alkaline salts are proton pump inhibitors developed by AstraZeneca. They are effective inhibitors of gastric acid secretion and, therefore, are useful for the prevention and treatment of gastric acid-related disorders and inflammatory gastrointestinal diseases (e.g., gastric ulcer, duodenal ulcer, reflux esophagitis and gastritis).

Various methods of preparing esomeprazole are described in the art. Among these methods, are the ones which involve resolving racemic omeprazole using an optical resolution agent and, preferred in terms of commercial applicability, are the methods which involve asymmetrically oxidizing a precursor of esomeprazole using a chiral reagent.

The main problem with the oxidation reaction to convert the sulfide intermediate into the sulfoxide compound is overoxidation, i.e. oxidation from sulfoxide to sulfone. The process of enantioselective oxidation, on increasing reaction scale, invariably leads to the formation of variable quantity of the sulfone impurity (cf. e.g. WO 2003/089408). The removal of sulfone impurity has often proved to be difficult with conventional purification methods such as crystallization, thus, time-consuming and costly processes must be carried out in order to obtain esomeprazole or its salts with high quality and quantity.

WO 1994/27988 describes the specific $Na^+$, $Mg^{2+}$, $Li^+$, $K^+$, $Ca^{2+}$, and $N(R)^{4+}$ salts of the two omeprazole enantiomers. In Example 1, esomeprazole sodium is prepared by reacting esomeprazole with sodium hydroxide using a mixture of methyl ethyl ketone and toluene from which the esomeprazole sodium precipitates. The subject matter related to esomeprazole sodium has been prosecuted in a divisional application of the corresponding European application EP 652872, which was published as EP 1020460.

In Example 11 of WO 1996/025235 esomeprazole sodium is prepared by reacting esomeprazole with sodium hydroxide in a mixture of methyl isobutyl ketone (MIK)/acetonitrile from which the esomeprazole sodium crystallizes.

In Example 41 of WO 2007/012650 esomeprazole sodium with deutered methoxy groups is prepared by reacting esomeprazole with sodium hydroxide in a mixture of methyl isobutyl ketone/isopropanol from which the esomeprazole sodium precipitates.

In Examples 1.1 to 1.3 of the International patent application WO 2006/001753 different solid forms of esomeprazole sodium are prepared by reacting esomeprazole with sodium hydroxide in a mixture of toluene/methanol, toluene/ethanol and toluene/isopropanol respectively.

Example 15 of WO 2008/149204 describes the preparation of esomeprazole sodium by dissolving esomeprazole in aqueous sodium hydroxide, extracting with methylene chloride, distilling-off the solvent, followed by addition of ethanol and distillation, addition of ethyl acetate and distillation, and final crystallization from ethyl acetate. Example 16 describes the preparation of esomeprazole sodium using sodium ethoxide as base and ethyl acetate as solvent.

Finally, Example 1-III of WO 2009/040825 describes the preparation of esomeprazole sodium by reacting esomeprazole with sodium hydroxide in methanol.

The preparation of the esomeprazole sodium in the conditions described in the previous documents show a low purification of esomeprazole sodium regarding the sulfone impurity with the exception of the process described in WO 2009/040825. However, it has been verified that the process described in this document yields to a methanol solvate. This fact shows the drawback that an additional step of converting the methanol solvate into the desolvated compound is needed. In addition, when desolvating the methanol solvate, the crystalline structure is lost and the esomeprazole sodium obtained is in amorphous form.

Thus, although there are known in the art several methods to prepare esomeprazole sodium which include crystallization or precipitation of the esomeprazole sodium from the reaction media, not good enough purification results are obtained regarding the sulfone impurity by crystallization/precipitation, a common technique used to purify organic compounds.

Other documents describe the preparation of esomeprazole sodium and isolation of the product by solvent evaporation, addition of a different solvent to the residue to isolate the esomeprazole sodium and filtering the product from the resulting suspension. However, these methods involving distilling-off completely the reaction solvent are not appropriate for industrial scale manufacture since they imply working with small volumes after solvent evaporation being often difficult to stir. They also involve problems of over-heating, problems of crude degradation, and problems related to the difficulty of removing the remaining solvent. In addition, it is necessary to carry out additional steps in order to isolate the final product. Among the documents where this type of isolation conditions are described are the following ones:

WO 2003/089408 describes the preparation of esomeprazole sodium by reaction of esomeprazole and aqueous sodium hydroxide or a sodium methoxide solution 30% w/v in methyl isobutyl ketone as solvent, distilling-off completely the solvent and then treating the obtained residue having the sulfone impurity with a solvent system comprising an organic solvent selected from ketone and nitrile in order to purify the sulfone impurity. According to the Examples, this purification is achieved by suspending the esomeprazole sodium first in acetonitrile and then in acetone.

WO 2004/052882 describes the preparation of esomeprazole sodium in water as solvent, followed by distilling-off the water and treating with acetonitrile.

WO 2004/002982 describes the reaction of esomeprazole and sodium hydroxide in methanol, distilling-off completely the solvent and then treating the solid obtained with diisopropyl ether.

WO 2007/013743 describes the treatment of a residue of esomeprazole sodium with a mixture of methyl isobutyl ketone and acetonitrile.

Finally, US 20070259921 describes several crystalline forms of esomeprazole sodium and processes for their preparation, some of them comprising the uses of ketones, alcohols and other solvents, and sodium bases. All the Examples describe processes involving distilling-off the reaction solvent before addition of another solvent.

Therefore, from what is known in the art it is derived that the provision of a purification process of esomeprazole sodium which remove the sulfone impurity and which proceeds with high yield, is still of great interest for the industrial manufacture of this compound.

SUMMARY

It has presently been found that the preparation of esomeprazole sodium from esomeprazole using a ($C_3$-$C_8$)-ketone or a mixture thereof, a sodium alcoxide, and a ($C_1$-$C_5$)-alcohol allows removing the sulfone impurity present in the esomeprazole crude, an impurity difficult to eliminate by the known reaction and precipitation conditions. This impurity is the result of the over-oxidation produced in the oxidation reaction of the sulfide group carried out in most of the processes known in the art for preparing 2-(2-pyridylmethylsulfinyl)-benzimidazole derivatives, in particular, esomeprazole.

The term sulfone impurity corresponds to the compound 5-methoxy-2-[(S)-[(4-methoxy-3,5-dimethyl-2-pyridinyl)methyl]sulfonyl]-1H-benzimidazole having the formula below.

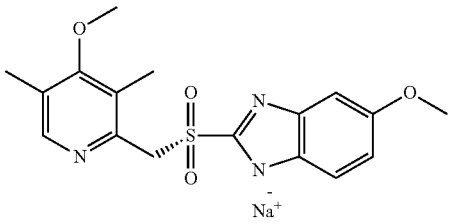

Likewise, esomeprazole sodium can also be purified by recrystallization in a mixture of at least one ($C_3$-$C_8$)-ketone and a ($C_1$-$C_5$)-alcohol.

These results regarding purification are achieved thanks to the specific conditions used, in particular, the combination of a ketone with an alcohol, and the fact that the process goes through a dissolution of the esomeprazole sodium in the solvent system employed, The selection of this specific conditions is considered an important contribution to the art, since although several attempts have been made in the art to purify the esomeprazole sodium from the sulfone impurity by precipitation from different solvents, none of them have succeeded in reducing drastically the sulfone levels.

Thus, the process of the present invention represents a simple and economic alternative to carry out the preparation of esomeprazole sodium substantially free of sulfone impurity, in general, with no need of additional purifications.

Therefore, the present invention relates to a preparation process of esomeprazole sodium substantially free of sulfone impurity, which means having a content of 5-methoxy-2-[(S)-[(4-methoxy-3,5-dimethyl-2-pyridinyl)methyl]sulfonyl]-1H-benzimidazole equal to or lower than 0.5% w/w, comprising the steps of: a) either combining esomeprazole with a ($C_3$-$C_8$)-ketone or a mixture thereof, a sodium alcoxide, and a ($C_1$-$C_5$)-alcohol; or combining esomeprazole sodium with a ($C_3$-$C_8$)-ketone or a mixture thereof, and a ($C_1$-$C_5$)-alcohol; and b) recovering the esomeprazole sodium formed from the reaction media by filtration. In particular, the process comprises $a_1$) combining a solution of esomeprazole in a ($C_3$-$C_8$)-ketone or a mixture thereof, with a sodium alcoxide, and a ($C_1$-$C_5$)-alcohol; or $a_2$) dissolving esomeprazole sodium with a ($C_3$-$C_8$)-ketone or a mixture thereof, and a ($C_1$-$C_5$)-alcohol to form a solution; and b) recovering the esomeprazole sodium formed, from the reaction media of step a) which comprises a ($C_3$-$C_8$)-ketone or a mixture thereof and a ($C_1$-$C_5$)-alcohol, by filtration.

DETAILED DESCRIPTION

The term "substantially free of sulfone impurity" denotes herein that the sulfone content in the esomeprazole sodium does not exceed 0.5% w/w of the salt which means that is equal to or lower than 0.5% w/w.

Preferably, the sulfone content does not exceed 0.3% w/w of the salt. More preferably, the sulfone content does not exceed 0.2% w/w of the salt. Even more preferably, the sulfone content does not exceed 0.1% w/w. Even still more preferably, the sulfone impurity is absent or not detected by analytical methods such as HPLC.

Preferably, a molar ratio of esomeprazole and sodium alkoxide comprised between 1:1 and 1:1.2 is used. More preferably, a molar ratio of 1:1 is used.

The sodium alkoxide can be used as a solid or as a solution in a ($C_1$-$C_5$)-alcohol. In a preferred embodiment, in step a) of the process of the present invention esomeprazole is combined with the ($C_3$-$C_8$)-ketone or a mixture thereof, a sodium alkoxide and a ($C_1$-$C_5$)-alcohol. In another preferred embodiment of the process, in step a) esomeprazole is combined with the ($C_3$-$C_8$)-ketone or a mixture thereof, and a solution of a sodium alkoxide in a ($C_1$-$C_5$)-alcohol. Preferably, the ($C_3$-$C_8$)-ketone is methyl isobutyl ketone.

In a more preferred embodiment of the process, the sodium alkoxide is selected from the group consisting of sodium methoxide, sodium ethoxide, sodium isopropoxide, sodium tert-butoxide, and sodium 1-pentoxide. Thus, the term sodium alkoxide refers to a ($C_1$-$C_5$)-alkoxide. In another more preferred embodiment of the process, the sodium ($C_1$-$C_5$)-alkoxide is selected from sodium methoxide, sodium ethoxide, and sodium tert-butoxide In still another more preferred embodiment of the process, the sodium ($C_1$-$C_5$)-alkoxide is sodium methoxide.

Examples of the ($C_1$-$C_5$)-alcohol include methanol, ethanol, n-propanol, isopropanol, n-butanol, isobutanol, tert-butanol, 2-methyl-1-butanol, isoamyl alcohol, and furfuryl alcohol. Preferably, a ($C_1$-$C_4$) alcohol is used. More preferably, the ($C_1$-$C_4$)-alcohol is methanol, ethanol, or tert-butanol. Even more preferably, the ($C_1$-$C_4$)-alcohol is methanol.

Examples of appropriate ($C_3$-$C_8$)-ketones include methyl isobutyl ketone, methyl ethyl ketone (MEK), acetone, or ciclohexanone. Preferred ketones are methyl isobutyl ketone, methyl ethyl ketone, and acetone.

Preferably, the amount of $(C_3$-$C_8)$-ketones/$(C_1$-$C_5)$-alcohol in respect of the starting esomeprazole is comprised between 3 and 18 ml/g.

Preferably, the amount of the $(C_3$-$C_8)$-ketones is comprised between 93-98% v/v of the total solvent and the amount of $(C_1$-$C_5)$-alcohol is comprised between 2%-7% v/v of the total solvent. More preferably, the amount of the $(C_3$-$C_8)$-ketones is comprised between 93-97% v/v of the total solvent and the amount of $(C_1$-$C_5)$-alcohol is comprised between 3%-7% v/v of the total solvent.

In a particular embodiment, the process involves dissolving the esomeprazole in a $(C_3$-$C_8)$-ketone, preferably methyl isobutyl ketone, followed by addition of the solution of the sodium alkoxide in the $(C_1$-$C_5)$-alcohol, occurring the formation of the esomeprazole sodium. Alternatively, solid sodium alkoxide and the $(C_1$-$C_5)$-alcohol can be used. The reaction can be carried out at a wide range of temperatures, in general between 10° C. and the reflux temperature of the solvent employed. Preferably, this particular embodiment of the process is carried out at room temperature. A suspension of esomeprazole sodium is obtained being the compound isolated from the reaction media by filtration.

In a particular embodiment, the $(C_3$-$C_8)$-ketone is selected from methyl isobutyl ketone, methyl ethyl ketone, and acetone, and the $(C_1$-$C_5)$-alcohol is methanol. Preferably, the amount of the methyl isobutyl ketone/methanol, methyl ethyl ketone/methanol or acetone/methanol is comprised between 4 and 10 ml/g of the starting esomeprazole. More preferably the amount is comprised between 6.5-7.5 ml/g. Preferably, the amount of methyl isobutyl ketone, methyl ethyl ketone, or acetone is 93-94% v/v of the total solvent and the amount of methanol 6%-7% v/v of the total solvent.

In a preferred embodiment of the process of the present invention, in step a) a mixture of methyl isobutyl ketone and acetone is used. In another preferred embodiment of the process, in step a) a mixture of methyl ethyl ketone and acetone is used. In these preferred embodiments, even a better purification of sulfone impurity can be obtained. In addition, it has been found that a high purification of the R-omeprazole impurity, when is present in the esomeprazole crude used as starting material, is also achieved.

The acetone can be added after adding the sodium alkoxide and the $(C_1$-$C_5)$-alcohol or before it. In a preferred embodiment, the acetone is added after combining the esomeprazole with methyl isobutyl ketone, the sodium alkoxide and the $(C_1$-$C_5)$-alcohol. In another preferred embodiment the acetone is added after combining the esomeprazole sodium with the methyl isobutyl ketone, and the $(C_1$-$C_5)$-alcohol.

In these embodiments where a mixture of methyl isobutyl ketone and acetone or a mixture of methyl ethyl ketone and acetone is used, preferably the $(C_1$-$C_5)$-alcohol is methanol. Also preferably, the total amount of methyl isobutyl ketone/acetone/methanol or the total amount of methyl ethyl ketone/acetone/methanol in respect of the starting esomeprazole is comprised between 7 and 18 ml/g. More preferably, the total amount of methyl isobutyl ketone/acetone/methanol is comprised between 10 and 15.5 ml/g, and even more preferably is 10 ml/g.

Also preferably, the mixture of methyl isobutyl ketone/acetone/methanol or the mixture of methyl ethyl ketone/acetone/methanol, comprise an amount of acetone between 20% and 60% v/v in respect of the total amount of solvent. More preferably, the amount of acetone in the mixture is comprised between 30% and 50% v/v. Even more preferably, the amount of acetone in the mixture is 50% v/v. Preferably, the amount of methanol is comprised between 2%-7% v/v in respect of the total amount of solvent. More preferably, the amount of methanol is comprised between 3%-6% v/v of the total solvent.

Depending on the concentration of the reaction mixture, the temperature, and the volume ratio between methyl isobutyl ketone/acetone/methanol or methyl ethyl ketone/acetone/methanol, the esomeprazole sodium solid is formed when adding the base or the acetone, or once the addition of the base or of the acetone has been completed.

The reaction can be carried out in a wide range of temperatures. Preferably, it is carried out at room temperature.

In another preferred embodiment, the preparation process of the present invention, further comprises the addition of an antisolvent selected from the group consisting of $(C_4$-$C_8)$-alkyl ethers such as methyl tert-butyl ether (MTBE) or isopropyl ether (iPr$_2$O), $(C_5$-$C_7)$-alkanes such as heptane or hexane, or $(C_6$-$C_7)$-cycloalkanes such as cyclohexane. By the addition of the antisolvent, a better yield is obtained without compromising the purification achieved. Preferably, the antisolvent is MTBE or iPr$_2$O.

The $(C_3$-$C_8)$-ketones/$(C_1$-$C_5)$-alcohol/antisolvent can be mixed with the esomeprazole in any order.

In a particular embodiment, the mixture of $(C_3$-$C_8)$-ketones/$(C_1$-$C_5)$-alcohol/antisolvent is methyl isobutyl ketone/acetone/methanol/antisolvent. Preferably, the total amount of solvent in this preferred embodiment is comprised between 8 and 21 ml/g of starting esomeprazole. More preferably, the total amount of solvent, in respect of the starting esomeprazole is comprised between 12 and 17 ml/g. Even more preferably, the total amount of solvent is comprised between 12 and 15 ml/g.

More preferably, the amount of acetone in respect of the total amount of solvent is comprised between 20% and 50% v/v. Even more preferably, the amount of acetone is comprised between 25% and 45% v/v. Even still more preferably, the amount of acetone is comprised between 40-45% v/v. Preferably, the amount of antisolvent in respect of the total amount of solvent is comprised between 8% and 30% v/v. More preferably, the amount of antisolvent is comprised between 10% and 25% v/v. Even more preferably, the amount of antisolvent is comprised between 10-15% v/v, and even still more preferably, the amount of antisolvent is comprised between 12-14% v/v. Preferably, the amount of methanol, is comprised between 2%-7% v/v in respect of the total amount of solvent. More preferably, the amount of methanol is comprised between 3%-6% v/v. Even more preferably, the amount of methanol is comprised between 3-4% v/v.

In another particular embodiment, the mixture of $(C_3$-$C_8)$-ketones/$(C_1$-$C_5)$-alcohol/antisolvent is acetone/methanol/antisolvent. In another particular embodiment, the mixture of $(C_3$-$C_8)$-ketones/$(C_1$-$C_5)$-alcohol/antisolvent is methyl isobutyl ketone/methanol/antisolvent. Preferably, the antisolvent is methyl tert-butyl ether. Also preferably, the amount of antisolvent in respect of the total amount of solvent is comprised between 8% and 30% v/v. More preferably, the amount of antisolvent is comprised between 10% and 25% v/v. Even more preferably, the amount of antisolvent is comprised between 10-15% v/v. Preferably, the amount of methanol, is comprised between 2-7% v/v in respect of the total amount of solvent. More preferably, the amount of methanol is comprised between 3-6% v/v of the total solvent. Even more preferably, the amount of methanol is 6% of the total solvent.

In general, the esomeprazole sodium formed is removed from the reaction media by filtration and subsequent washings of the filtrated solid. The isolated esomeprazole sodium is thereafter dried in order to remove the solvent.

High contents of sulfone can be effectively removed by the process of the present invention. When the sulfone contents of the starting material are higher than 2%, an additional purification step could be needed. Thus, in cases of highly impurified esomeprazole crude an additional recrystallization of the esomeprazole sodium obtained by the process of the present invention in the solvent conditions described in this patent application can be carried out in order to obtain a compound having a sulfone content in accordance with pharmacopeia specifications (sulfone content equal or less than 0.2%).

Therefore, the recrystallization can be carried out by combining esomeprazole sodium with a ($C_3$-$C_8$)-ketone or a mixture thereof, and a ($C_1$-$C_5$)-alcohol. The following particular embodiment is illustrative of the general process of recrystallization according to the invention.

In a particular embodiment, the recrystallization is carried out by dissolving esomeprazole sodium with a mixture of methyl isobutyl ketone/($C_1$-$C_5$)-alcohol or in a mixture of methyl isobutyl ketone/($C_1$-$C_5$)-alcohol/acetone at a temperature where the esomeprazole sodium is solubilized, which depends on the combination of solvents and the proportions of each of them, followed by cooling the solution, preferably at room temperature in order to obtain the esomeprazole sodium. It is often necessary to remove part of the solvent before cooling, in order to form the esomeprazole sodium. Generally, the solvent is removed until a suspension is obtained.

Preferably, the ($C_1$-$C_5$)-alcohol is methanol or 1-propanol. More preferably, the ($C_1$-$C_5$)-alcohol is methanol.

In a preferred embodiment, methyl isobutyl ketone and methanol are used as solvents, being the initial amount of methyl isobutyl ketone/methanol comprised between 10-20 ml/g of starting esomeprazole sodium, preferably 13 ml/g. Also preferably, the mixture of methyl isobutyl ketone/methanol comprises an amount of methanol of 25% of the total solution.

In another preferred embodiment, methyl isobutyl ketone and 1-propanol are used as solvents, being the initial amount of methyl isobutyl ketone/1-propanol comprised between 10-20 ml/g of starting esomeprazole sodium, preferably 14 ml/g. Also preferably, the mixture of methyl isobutyl ketone/1-propanol comprises an amount of 1-propanol of 29% of the total solution.

The previous recrystallisation in the solvent composition of the present invention can also be used to diminish the sulfone impurity and also the R-omeprazole impurity of esomeprazole sodium obtained by other processes known in the art. Preferably, the R-omeprazole impurity content does not exceed 0.5% w/w of the salt which means that is equal to or lower than 0.5% w/w. More preferably, the R-omeprazole content does not exceed 0.2% w/w of the salt. Even more preferably, the R-omeprazole content does not exceed 0.1% w/w. Even still more preferably, the R-omeprazole impurity is absent or not detected by analytical methods such as HPLC.

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

The purity of the esomeprazole sodium has been determined by HPLC. The HPLC conditions described in the U.S. Pharmacopeia (USP32) for the determination of the sulfone content and for the determination of the R-enantiomer content in the magnesium esomeprazole can be used to determine the sulfone content and the R-enantiomer content in the esomeprazole sodium obtained by the process of the present invention. The particular conditions to be used are described on sections chromatographic purity and enantiomeric purity of the USP32 respectively.

For the purposes of the invention, the ketones used may contain water in the usual amounts found in the ketones commercialized at industrial scale.

Example 1

Preparation of Esomeprazole Sodium Using Methyl Isobutyl Ketone as Solvent and a Solution of Sodium Methoxide in Methanol 30% sodium methoxide in methanol (4.7 mL, 25.3 mmol) was added dropwise at room temperature to a solution of esomeprazole (8.5 g, 24.6 mmol; 2.2% sulfone) in methyl isobutyl ketone (60 mL). The resulting slurry was stirred overnight. The solid was collected by filtration, rinsed with methyl isobutyl ketone (2×10 mL) and dried under reduced pressure at 50° C. to yield esomeprazole sodium. Yield: 6.3 g (70%). Sulfone content: 0.33%.

Example 2

Preparation of Esomeprazole Sodium Using Methyl Isobutyl Ketone/Acetone and a Solution of Sodium Methoxide in Methanol 30% sodium methoxide in methanol (4.7 mL, 25.3 mmol) was added dropwise to a solution of esomeprazole (8.5 g, 24.6 mmol; 2.2% sulfone, 4.7% R-enantiomer) in methyl isobutyl ketone (60 mL). The mixture was stirred for 15 min. Acetone (60 mL) was added in 30 min. The resulting slurry was stirred overnight at room temperature. The solid was collected by filtration, rinsed with acetone (2×10 mL) and dried under reduced pressure at 50° C. to yield esomeprazole sodium. Yield: 5.5 g (61%). Sulfone content: 0.17%. R-enantiomer content: 0.00%.

Example 3

Preparation of Sodium Esomeprazole Using Methyl Isobutyl Ketone/Acetone and a Solution of Sodium Methoxide in Methanol 30% sodium methoxide in methanol (6.0 mL, 32.3 mmol) was added dropwise to a solution of esomeprazole (10.7 g, 31.0 mmol; 1.1% sulfone, 2.5% R-enantiomer) in methyl isobutyl ketone (75 mL). The mixture was stirred for 20 min. Acetone (75 mL) was added in 30 min. The resulting slurry was stirred overnight at room temperature. The solid was collected by filtration, rinsed with acetone (2×12.5 mL) and dried under reduced pressure at 50° C. to yield esomeprazole sodium. Yield: 6.8 g (60%). Sulfone content: 0.06%. R-enantiomer content: 0.00%

Example 4

Preparation of Esomeprazole Sodium Using Methyl Isobutyl Ketone/Acetone and a Solution of Sodium Methoxide in Methanol Acetone (75 mL) was added to a solution of esomeprazole (10.1 g, 29.2 mmol; 1.1% sulfone, 2.5% R-enantiomer) in methyl isobutyl ketone (75 mL). 30% sodium methoxide in methanol (5.7 mL, 30.7 mmol) was added in 15 min. The resulting slurry was stirred overnight at room temperature. The solid was collected by filtration, rinsed with acetone (2×12 mL) and dried under reduced pressure at 50° C. to yield esomeprazole sodium. Yield: 6.5 g (61%) Sulfone content: 0.06%. R-enantiomer content: 0.00%.

Example 5

Preparation of Esomeprazole Sodium Using Methyl Isobutyl Ketone/Acetone and a Solution of Sodium Methoxide in Methanol A solution of esomeprazole (9.5 g, 27.5 mmol; 2.3% sulfone) in methyl isobutyl ketone (60 mL) was cooled to 15° C. 30% sodium methoxide in methanol (5.2 mL, 28.0 mmol) was added in 15 min. The addition funnel was rinsed with MeOH (0.3 mL) and methyl isobutyl ketone (0.7 mL). The mixture was stirred for 15 min and acetone (30 mL) was added slowly over 20 min. Subsequently, the solution was stirred at 25° C. A solid started to crystallize. The resulting slurry was stirred overnight. The solid was collected by filtration, rinsed with acetone (2×15 mL) and dried under reduced pressure at 50° C. to yield esomeprazole sodium. Yield: 6.1 g (60%). Sulfone content: 0.20%.

Example 6

Preparation of Esomeprazole Sodium Using Methyl Isobutyl Ketone/Acetone/Methyl-Tert-Butylether and a Solution of Sodium Methoxide in Methanol A solution of esomeprazole (9.5 g, 27.5 mmol; 2.3% sulfone, 2.3% R-enantiomer) in methyl isobutyl ketone (60 mL) was cooled to 15° C. 30% sodium methoxide in methanol (5.2 mL, 28.0 mmol) was added in 15 min. The addition funnel was rinsed with MeOH (0.3 mL) and methyl isobutyl ketone (0.7 mL). The mixture was stirred for 15 min and acetone (60 mL) was added slowly over 15 min. Subsequently, the solution was stirred at 25° C. A solid started to crystallize. After 1 h stirring, methyl tert-butyl ether (15 mL) was added dropwise. The resulting slurry was stirred overnight. The solid was collected by filtration, rinsed with acetone (2×15 mL) and dried under reduced pressure at 50° C. to yield esomeprazole sodium. Yield: 6.3 g (62%). Sulfone content: 0.23%.

Example 7

Preparation of Esomeprazole Sodium Using Methyl Isobutyl Ketone/Methanol/Acetone/Methyl-Tert-Butylether and Sodium Tert-Butoxide A solution of esomeprazole (4.7 g, 13.6 mmol; 2.3% sulfone, 2.3% R-enantiomer) in methyl isobutyl ketone (30 mL) and methanol (2.1 mL) was cooled to 15° C. Sodium tert-butoxide (1.33 g, 13.8 mmol) was added in 5 min and the mixture stirred for 15 min. To the resulting solution, acetone (30 mL) was added slowly over 15 min and a solid started to crystallize. The mixture was heated to 25° C. and methyl tert-butyl ether (7.5 mL) was added dropwise. The slurry was stirred overnight. The solid was collected by filtration, rinsed with acetone (2×5 mL) and dried under reduced pressure at 50° C. to yield esomeprazole sodium. Yield: 3.2 g (65%). Sulfone content: 0.26%. R-enantiomer content: 0.01%

Example 8

Preparation of Esomeprazole Sodium Using Methyl Isobutyl Ketone/Acetone/Diisopropylether and a Solution of Sodium Methoxide in Methanol A solution of esomeprazole (4.4 g, 12.7 mmol; 2.3% sulfone) in methyl isobutyl ketone (28 mL) was cooled to 15° C. 30% sodium methoxide in methanol (2.4 mL, 12.9 mmol) was added dropwise. The mixture was stirred for 15 min and acetone (28 mL) was added slowly over 15 min. Subsequently, the solution was stirred at 25° C. A solid started to crystallize. Diisopropyl ether (7.5 mL) was added dropwise and the resulting slurry was stirred overnight. The solid was collected by filtration, rinsed with acetone (2×5 mL) and dried under reduced pressure at 50° C. to yield esomeprazole sodium. Yield: 3.2 g (68%). Sulfone content: 0.22%.

Example 9

Preparation of Esomeprazole Sodium Using Methyl Isobutyl Ketone/Acetone/Methyl-Tert-Butylether and a Solution of Sodium Methoxide in Methanol A solution of esomeprazole (18.8 g, 54.4 mmol; 2.0% sulfone) in methyl isobutyl ketone (120 mL) was cooled to 15° C. 30% sodium methoxide in methanol (10.3 mL, 55.5 mmol) was added in 15 min. The mixture was stirred for 15 min and acetone (60 mL) was added slowly over 10 min. Subsequently, the solution was stirred at 26° C. A solid started to crystallize. After 20 min stirring, methyl tert-butyl ether (30 mL) was added dropwise. The resulting slurry was stirred overnight. The solid was collected by filtration, rinsed with acetone (2×20 mL) and dried under reduced pressure at 50° C. to yield esomeprazole sodium. Yield: 14.4 g (72%). Sulfone content: 0.19%.

Example 10

Preparation of Esomeprazole Sodium Using Methyl Isobutyl Ketone/Acetone/Methyl-Tert-Butylether and a Solution of Sodium Methoxide in Methanol Esomeprazole sodium was prepared from esomeprazole crude (14.3 g, 41.4 mmol; 2.3% sulfone) following the Example 6 but adding double quantity of methyl tert-butylether (45 mL). Yield: 10.6 g (70%). Sulfone content: 0.29%.

Example 11

Preparation of Esomeprazole Sodium Using Methyl Isobutyl Ketone/Acetone/Methyl-Tert-Butylether and a Solution of Sodium Methoxide in Methanol Esomeprazole sodium was prepared from esomeprazole crude (14.3 g, 41.4 mmol; 2.3% sulfone) following the Example 9 but adding double quantity of methyl tert-butylether (45 mL). Yield: 11.9 g (78%). Sulfone content: 0.39%.

Example 12

Recrystallization of Esomeprazole Sodium from a Mixture of Methyl Isobutyl Ketone/Methanol Esomeprazole sodium (3.0 g, 0.57% sulfone) was dissolved in methanol (10 ml, 3.3 ml/g) at 55° C. and methyl isobutyl ketone (30 ml, 10 ml/g) was added. The solution was concentrated under vacuum until a suspension is obtained. The esomeprazole sodium precipitates and the resulting slurry was stirred for 3 hours at room temperature. The solid was collected by filtration, rinsed with methyl isobutyl ketone (2×3 mL) and dried under reduced pressure at 50° C. to yield esomeprazole sodium. Yield: 2.16 g (72%). Sulfone content: 0.20%.

Example 13

Recrystallization of Esomeprazole Sodium from a Mixture of Methyl Isobutyl Ketone/1-Propanol Esomeprazole sodium (3.0 g, 0.36% sulfone) was dissolved in 1-propanol (12 ml) at 90-100° C. and methyl isobutyl ketone (30 ml) was added. The solution was concentrated under vacuum until a suspension is obtained, the remaining volume being approximately 60% of the initial volume. The esomeprazole sodium precipitates and the resulting slurry was stirred overnight. The solid was collected by filtration, rinsed with methyl isobutyl ketone (2×3 mL) and dried under reduced pressure at 50° C. to yield esomeprazole sodium. Yield: 2.16 g (72%). Sulfone content: 0.09%.

Example 14

Preparation of Esomeprazole Sodium Using Acetone and a Solution of Sodium Methoxide in Methanol A solution of esomeprazole (19.5 g, 56.5 mmol; 1.3% sulfone, 1.05% R-enantiomer) in acetone (120 mL) was cooled to 15° C. 30% sodium methoxide in methanol (10.7 mL, 57.6 mmol) was added in 15 min. Subsequently, the solution was stirred at 28° C. A solid started to crystallize. The resulting slurry was stirred overnight at room temperature. The solid was collected by filtration, rinsed with acetone (2×20 mL) and dried under reduced pressure at 50° C. to yield esomeprazole sodium. Yield: 10.6 g (51%). Sulfone content: 0.06%. R-enantiomer content: 0.02%

Example 15

Preparation of Esomeprazole Sodium Using Methyl Ethyl Ketone and a Solution of Sodium Methoxide in Methanol A solution of esomeprazole (19.5 g, 56.5 mmol; 1.3% sulfone, 1.05% R-enantiomer) in methyl ethyl ketone (120 mL) was cooled to 15° C. 30% sodium methoxide in methanol (10.7 mL, 57.6 mmol) was added in 15 min. Subsequently, the solution was stirred at 27° C. A solid started to crystallize. The resulting slurry was stirred overnight at room temperature. The solid was collected by filtration, rinsed with methyl ethyl ketone (2×20 mL) and dried under reduced pressure at 50° C. to yield esomeprazole sodium. Yield: 12.4 g (60%). Sulfone content: 0.06%. R-enantiomer content: 0.00%.

Example 16

Preparation of Esomeprazole Sodium Using Acetone/Methyl Ethyl Ketone and a Solution of Sodium Methoxide in Methanol A solution of esomeprazole (19.5 g, 56.5 mmol; 1.3% sulfone, 1.05% R-enantiomer) in methyl ethyl ketone (60 mL) and acetone (60 mL) was cooled to 15° C. 30% sodium methoxide in methanol (10.7 mL, 57.6 mmol) was added in 15 min. Subsequently, the solution was stirred at 27° C. A solid started to crystallize. The resulting slurry was stirred overnight at room temperature. The solid was collected by filtration, rinsed with acetone (2×20 mL) and dried under reduced pressure at 50° C. to yield esomeprazole sodium. Yield: 10.8 g (52%). Sulfone content: 0.05%. R-enantiomer content: 0.00%.

Example 17

Preparation of Esomeprazole Sodium Using Acetone/Methyl Tert-Butyl Ether and a Solution of Sodium Methoxide in Methanol A solution of esomeprazole (5.3 g, 15.3 mmol; 1.3% sulfone, 1.05% R-enantiomer) in acetone (33 mL) was cooled to 15° C. 30% sodium methoxide in methanol (2.9 mL, 15.6 mmol) was added in 15 min. Subsequently, the solution was stirred at 28° C. A solid started to crystallize. After 30 min stirring, methyl tert-butyl ether (6 mL) was added dropwise. The resulting slurry was stirred overnight at room temperature. The solid was collected by filtration, rinsed with acetone (2×6 mL) and dried under reduced pressure at 50° C. to yield esomeprazole sodium. Yield: 3.5 g (62%). Sulfone content: 0.28%. R-enantiomer content: 0.17%.

Example 18

Comparative Results Between Esomeprazole Sodium Obtained by the Process of the Present Invention and Esomeprazole Sodium Obtained by Reproduction of the Examples Known from the Prior Art The esomeprazole crude used to carry out the comparative examples had a contain of sulfone impurity of 2.3% according to HPLC. Example 41 of WO2007012650 was reproduced using esomeprazole instead deutered esomeprazole.

Table 1 shows the results obtained regarding the purification of the esomeprazole sodium from the sulfone impurity by reproduction of the process described in the prior art encompassing a crystallization/precipitation step from the reaction media.

TABLE 1

Comparative Examples

| Reproduction Examples of the prior art (comparative examples) | Reaction conditions | Sulfone % in the esomeprazole starting material | Sulfone % in esomeprazole sodium | Yield % | Observations |
|---|---|---|---|---|---|
| WO9427988 ex. 1 | MEK/toluene/NaOH 5M aq | | | | No precipitation is observed |
| U.S. Pat. No. 6,262,085 ex. 16 | MEK/toluene/NaOH 5M aq + seeding + solvent elimination | 2.3 | 1.90 | 86 | — |
| WO9602535 ex. 11 | MIK/NaOH 50% aq/ACN + distillation | 2.3 | 0.55 | 50 | — |
| WO2007012650 ex. 41 | MIK/IPA/NaOH 40% aq | 2.3 | 0.47 | 2 | — |
| WO20080149204 ex. 16 | AcOEt/EtONa | 2.3 | 1.4 | 72 | — |
| WO2009040825 | MeOH/NaOH | 2.3 | 0.28 | 79 | See comment below |
| WO2006001753 ex. 1.1 | toluene/MeOH/NaOH 45% aq | 2.3 | — | — | No precipitation is observed, even after partially concentration of the solution |
| WO2006001753 ex. 1.2 | toluene/EtOH/NaOH 45% aq | 2.3 | 2.2% | 90% | No precipitation is observed in the conditions described. The product crystallizes after partially concentration of the solution |
| WO2006001753 ex. 1.3 | toluene/IPA/NaOH 45% aq | 2.3 | 2.1% | 80% | No precipitation is observed in the conditions described. The product crystallizes after partially concentration of the solution |

In the reproduction of WO 2009040825 a methanol solvate was obtained. It has been verified by the present inventors that when desolvating the methanol solvate, the crystalline structure is lost and the esomeprazole sodium obtained is in amorphous form The results obtained following the preparation process of the present invention regarding the purification of the esomeprazole sodium from the sulfone impurity are included in Table 2.

TABLE 2

Examples of the present invention

| Examples | Solvent composition | Sulfone % in the esomeprazole starting material | Sulfone % in esomeprazole sodium | Yield % |
|---|---|---|---|---|
| Example 1 | MIK/methanol | 2.2 | 0.33 | 70 |
| Example 2 | MIK/acetone/methanol | 2.2 | 0.17 | 61 |
| Example 3 | MIK/acetone/methanol | 1.1 | 0.06 | 60 |
| Example 4 | MIK/acetone/methanol | 1.1 | 0.06 | 61 |
| Example 5 | MIK/acetone/methanol | 2.3 | 0.20 | 60 |
| Example 6 | MIK/acetone/methanol/MTBE | 2.3 | 0.23 | 62 |
| Example 7 | MIK/acetone/methanol/MTBE | 2.3 | 0.26 | 65 |
| Example 8 | MIK/acetone/methanol/iPr$_2$O | 2.3 | 0.22 | 68 |
| Example 9 | MIK/acetone/methanol/MTBE | 2.3 | 0.19 | 72 |
| Example 10 | MIK/acetone/methanol/MTBE | 2.3 | 0.29 | 70 |
| Example 11 | MIK/acetone/methanol/MTBE | 2.3 | 0.39 | 78 |
| Example 12 | MIK/methanol | 0.57 | 0.20 | 72 |
| Example 13 | MIK/1-propanol | 0.36 | 0.09 | 72 |
| Example 14 | Acetone/methanol | 1.3 | 0.06 | 51 |
| Example 15 | MEK/methanol | 1.3 | 0.06 | 60 |
| Example 16 | MEK/acetone/methanol | 1.3 | 0.05 | 52 |
| Example 17 | Acetone/methanol/MTBE | 1.3 | 0.28 | 62 |

Comparative Example 19

Esomeprazole Sodium Obtained by Reproduction of the Example 3 and 4 of WO 03/89408

It was reproduced Example 3 of WO 03/89408 in which esomeprazole sodium is purified by suspending esomeprazole sodium in acetone (10 volumes). Then, the dispersion is heated at reflux for 1 hour and cooled to 35-38° C. in order to recover the esomeprazole sodium.

It was also reproduced Example 4 of WO 03/89408 in which esomeprazole sodium is purified by suspending esomeprazole sodium in acetone (10 volumes) and aqueous NaCl. The ratio of acetone:aqueous NaCl being 99.3:0.7 v/v, and the concentration of NaCl in water is 5%). Then, the dispersion is heated at reflux for 1 hour and cooled to 35-38° C. in order to recover the esomeprazole sodium.

The results of the reproductions are summarized in Table 3.

TABLE 3

| Reproduction Examples of the prior art (comparative examples) | Sulfone impurity % in starting material esomeprazole sodium | Conditions | T | Sulfone impurity % | Yield |
|---|---|---|---|---|---|
| WO 03/89408 Reproduction Example 3 | 4.4 | acetone 10 vol. | 60° C. | 4.6 | 88% |
| WO 03/89408 Reproduction Example 4 | 4.4 | acetone/ NaCl 5% aq. 99.3:0.7 v/v | 60° C. | 4.1 | 74% |

Unlike what it is stated in WO 03/89408, the reproduction of the Examples 3 and 4 carried out by the present inventors has not allowed to remove the sulfone impurity.

Comparative Example 20

Effect of the Alcohol Present in the Solvent System of the Present Invention in the Purification of the Esomeprazole Sodium Table 4 shows the results of several assays carried out using a solvent system of the invention but in the absence of the alcohol in order to show the effect of the specific combination of solvents in the purification of esomeprazole sodium.

Each of the Examples was carried out with 10 g of esomeprazole, 60 ml of methylisobutylketone, 60 ml of acetone and 15 ml of methyl tert-butyl ether at a temperature of 25° C. Example 20A with 0.75 g of MeONa solid (1.02 eq.), Example 20B with 0.94 g EtONa solid (1.02 eq.), and Example 20C with 1.375 g of tBuONa solid (1.02 eq).

TABLE 4

| Comparative Examples | Sulfone impurity % in starting material esomeprazole sodium | Conditions | Sulfone impurity % | Yield |
|---|---|---|---|---|
| Comparative Example 20A | 2.3% | MIK/acetone/ MTBE 6:6:1.5 MeONa | 1.6% | 59% |
| Comparative Example 20B | 2.3% | MIK/acetone/ MTBE 6:6:1.5 EtONa | 1.9% | 86% |
| Comparative Example 20C | 2.3% | MIK/acetone/ MTBE 6:6:1.5 BuONa | 2.0% | 92% |

In the absence of an alcohol in the solvent system of the invention, the sulfone impurity is scarcely purified. Therefore, these results illustrate the influence of the specific combination of solvents according to the invention, on the purification of esomeprazole sodium. In particular the combination must comprise at least a $(C_3-C_8)$-ketone and a $(C_1-C_5)$-alcohol.

REFERENCES CITED IN THE DESCRIPTION

WO 2003/089408
WO 1994/27988
WO 1996/025235
WO 2007/012650
WO 2006/001753
WO 2008/149204
WO 2009/040825
WO 2004/052882
WO 2004/002982
WO 2007/013743
US 20070259921

The invention claimed is:

1. A preparation process of esomeprazole having a content of 5-methoxy-2-[(S)-[(4-methoxy-3,5-dimethyl-2-pyridinyl)methyl]sulfonyl]-1H-benzimidazole equal to or lower than 0.5% w/w comprising the steps of:
    a) either $a_1$) combining a solution of esomeprazole in a $(C_3-C_8)$-ketone or a mixture thereof, with a sodium alkoxide, and a $(C_1-C_5)$-alcohol; or $a_2$) dissolving esomeprazole sodium with a $(C_3-C_8)$-ketone or a mixture thereof, and a $(C_1-C_5)$-alcohol to form a solution; and
    b) recovering the esomeprazole sodium formed, from the reaction media of step a) which comprises a $(C_3-C_8)$-ketone or a mixture thereof and a $(C_1-C_5)$-alcohol, by filtration.

2. The preparation process according to claim 1, wherein in the step $a_1$) the amount of $(C_1-C_5)$-alcohol is comprised between 2-7% v/v.

3. The preparation process according to claim 2, wherein step a) comprises combining a solution of esomeprazole in a $(C_3-C_8)$-ketone or a mixture thereof, with a sodium alkoxide, and a $(C_1-C_5)$-alcohol.

4. The preparation process according to claim 3, wherein in step a) a solution of a sodium alkoxide in a $(C_1-C_5)$-alcohol is used.

5. The preparation process according to claim 2, wherein the $(C_3-C_8)$-ketone is selected from the group consisting of methyl isobutyl ketone, methyl ethyl ketone, and acetone.

6. The preparation process according to claim 2, wherein the sodium alkoxide is selected from the group consisting of sodium methoxide, sodium ethoxide, and sodium tert-butoxide.

7. The preparation process according to claim 6, wherein the sodium alkoxide is sodium methoxide.

8. The preparation process according to claim 2, wherein the $(C_1-C_5)$-alcohol is selected from the group consisting of methanol, ethanol, and tert-butanol.

9. The preparation process according to claim 8, wherein the $(C_1-C_5)$-alcohol is methanol.

10. The preparation process according to claim 1, wherein in step a) a mixture of methyl isobutyl ketone/acetone is used.

11. The preparation process according to claim 10, wherein the total amount of solvent is comprised between 7 and 18 ml/g of starting esomeprazole and the amount of acetone is comprised between 20 and 60% v/v in respect of the total amount of solvent.

12. The preparation process according to claim 10, wherein the acetone is added after combining the esomeprazole with methyl isobutyl ketone, sodium alkoxide, and a $(C_1-C_5)$-alcohol, or after combining the esomeprazole sodium with methyl isobutyl ketone and a $(C_1-C_5)$-alcohol.

13. The preparation process according to claim 1, further comprising the addition of an antisolvent selected from the group consisting of $(C_4-C_8)$-alkyl ethers, $(C_5-C_7)$-alkanes, and $(C_6-C_7)$-cycloalkanes.

14. The preparation process according to claim 13, wherein the antisolvent is methyl tert-butyl ether or isopropyl ether.

15. The preparation process according to claim 13, wherein a mixture methyl isobutyl ketone/acetone is used.

16. The preparation process according to claim 13, wherein the amount of antisolvent in respect of the total amount of solvent is comprised between 10-25% v/v and the amount of acetone in respect of the total amount of solvent is comprised between 20% and 50% v/v.

17. The preparation process according to claim 1, wherein step a) comprises combining a solution of esomeprazole in a $(C_3-C_8)$-ketone or a mixture thereof, with a sodium alkoxide, and a $(C_1-C_5)$-alcohol.

18. The preparation process according to claim 17, wherein the $(C_3-C_8)$-ketone is selected from the group consisting of methyl isobutyl ketone, methyl ethyl ketone, and acetone.

19. The preparation process according to claim 18, wherein the $(C_1-C_5)$-alcohol is selected from the group consisting of methanol, ethanol, and tert-butanol.

20. The preparation process according to claim 19, wherein the sodium alkoxide is selected from the group consisting of sodium methoxide, sodium ethoxide, and sodium tert-butoxide.

\* \* \* \* \*